United States Patent [19]
Clemens

[11] 4,119,406
[45] Oct. 10, 1978

[54] CALIBRATION APPARATUS

[75] Inventor: Anton Hubert Clemens, Elkhart, Ind.

[73] Assignee: Miles Laboratories, Inc., Elkhart, Ind.

[21] Appl. No.: 683,806

[22] Filed: May 6, 1976

[51] Int. Cl.² .......................... A61B 5/00; G01N 1/00; G01N 33/16

[52] U.S. Cl. .................................. 422/81; 23/230 R; 128/2 F; 137/597; 422/68; 422/99

[58] Field of Search .................. 23/253 R, 259, 253 A, 23/230 A, 230 R; 128/DIG. 5, 2 G, 2.05 D, 2 F, 2.05 R, 214 E; 137/597

[56] References Cited

U.S. PATENT DOCUMENTS

| | | | |
|---|---|---|---|
| 2,335,032 | 11/1943 | Sullivan | 23/255 E X |
| 3,230,048 | 1/1966 | Skeggs | 23/253 R |
| 3,425,807 | 2/1969 | Levy | 23/232 R |
| 3,560,161 | 2/1971 | Webb | 23/230 R |
| 3,607,073 | 9/1971 | Stamm | 23/253 R X |
| 3,690,833 | 9/1972 | Ferrari | 23/230 X |
| 3,838,682 | 10/1974 | Clark et al. | 128/214 E X |

*Primary Examiner*—Robert M. Reese
*Attorney, Agent, or Firm*—Louis E. Davidson

[57] ABSTRACT

Calibration apparatus is described for use in a calibratable analytical system wherein a continuously flowing liquid sample, either alone or in admixture with other liquids, is normally caused to contact a sensor. The novel calibration apparatus enables diversion of said continuously flowing sample out of contact with the sensor and alternate contact of a calibration reference liquid or other calibration sample with the sensor. The calibration apparatus of the present invention is particularly useful in a system for analytical monitoring of a continuously flowing liquid blood sample obtained through a double lumen cannula inserted into a blood vessel of a human or animal subject. This apparatus permits the analytical system to be calibrated without the necessity of removing any portion of the cannula from the subject thereby avoiding the risk of loss of sterility inherent in such removal.

2 Claims, 5 Drawing Figures

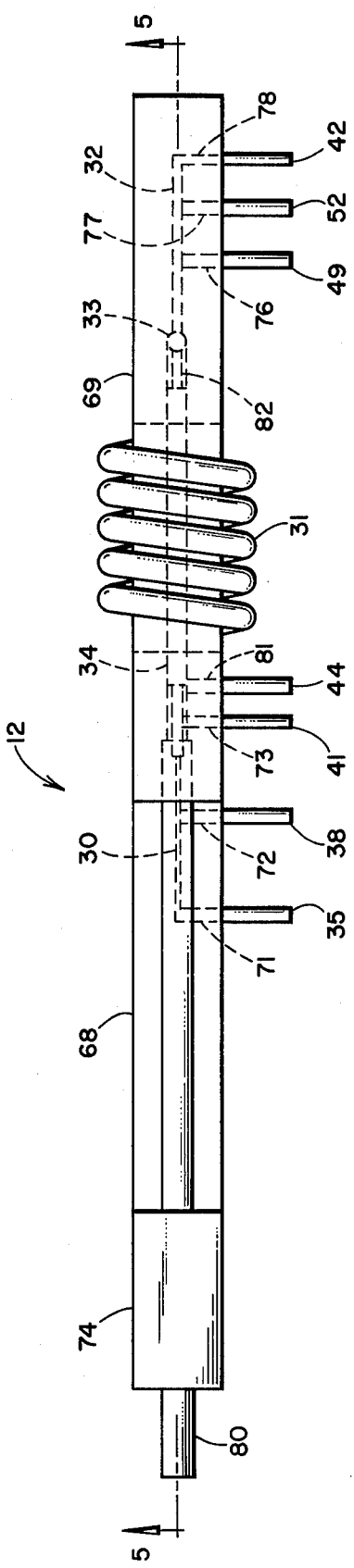
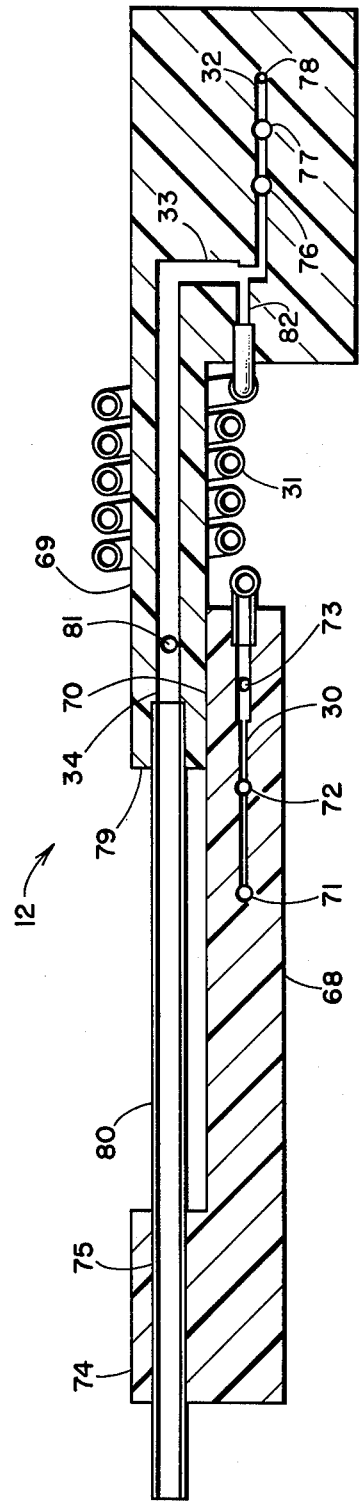
FIG. 4
FIG. 5

CALIBRATION APPARATUS

BACKGROUND AND PRIOR ART

Sensors, such as glucose sensors, for detecting and measuring desired characteristics, such as glucose content, of liquid samples are well-known. Whenever these sensors need to be calibrated, the liquid sample which normally contacts the sensor is replaced with one or more reference liquids or calibration samples. While this is usually a simple procedure, it can present complications when the analysis is being conducted on blood from human or animal subjects. In a typical situation for continuous blood sampling, a double lumen catheter is inserted into a cannula positioned in a vein or artery of the subject. The double lumen catheter is connected through appropriate pumping apparatus to a sensor. In the prior art, whenever the sensor needed calibration, the double lumen catheter would be removed from the cannula and inserted into a container having a desired reference liquid therein. After the calibration is finished, the double lumen catheter is then replaced in the cannula for further analytical use. This prior art procedure can have the disadvantage of losing the desired sterility conditions for the catheter and cannula. It also has the disadvantage that the cannula may become clogged with coagulated blood while the catheter is removed. The cannula would then have to be flushed or replaced with attendant discomfort to the patient.

There is thus a need for apparatus for calibration of a sensor during use which does not interfere with the usual sampling procedure.

SUMMARY OF THE INVENTION

In accordance with the present invention, apparatus is provided for calibration of a sensor during use in a calibratable system for monitoring a specific characteristic of a continuously flowing liquid sample comprising in combination a sensor for detecting said specific characteristic, said sensor having flow path means; and flow diversion means connected to said sensor flow path means, said flow diversion means being adapted for communication with a source of continuously flowing sample to be monitored and to a source of reference liquid, said flow diversion means having a normal operating position in which it is adapted to enable a continuously flowing sample from a source connected thereto to be channeled through said sensor flow path means, said flow diversion means also having a calibrating position in which it is adapted to cause diversion of such continuously flowing sample away from said sensor flow path means and alternatively to cause a reference fluid from a source connected thereto to be introduced into said sensor flow path means.

DESCRIPTION OF THE DRAWINGS

FIG. 4 is a plan view of a preferred manifold useful in an analytical system employing the calibration apparatus of the present invention; and FIG. 5 is a vertical cross-sectional view of the manifold taken along line 5—5 of FIG. 4.

DESCRIPTION OF THE INVENTION

Figure 1:
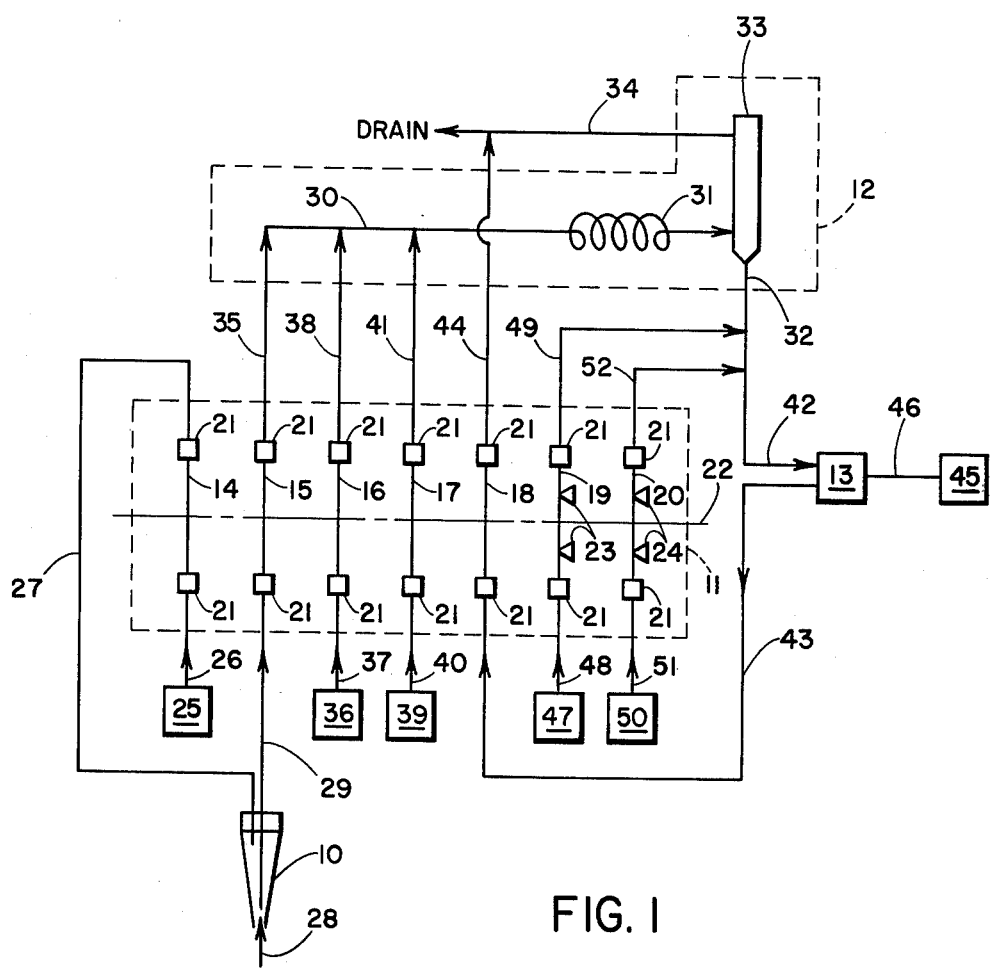
FIG. 1 is a schematic drawing of an analytical system incorporating one form of the calibration apparatus of the present invention.

With reference to FIG. 1, an analytical system is described for determining a desired characteristic, such as glucose, in a blood sample from a human or animal subject. This system comprises a double lumen cannula 10, a seven-channel peristaltic pump 11, a manifold 12, a sensor 13, read-out means 45 and associated piping. While a seven-channel peristaltic pump is described for illustrative purposes, it is understood that a combination of separate pumps having the equivalent of a total of more or less than seven channels can be used. Pumping means other than peristaltic pumps can also be used.

The various channels of pump 11 are represented by lines 14, 15, 16, 17, 18, 19 and 20 which are each supported within the pump by sleeves 21. The pumping elements of pump 11 are ganged along a common shaft shown schematically by axis 22. Lines 14, 15, 16, 17 and 18 are intended for continuous pumping action. Lines 19 and 20 are intended for intermittent operation. Clamps 23 for line 19 and clamps 24 for line 20 schematically represent means for sealing or closing lines 19 and 20 whenever it is desired to stop flow through these lines by interrupting the pumping action on these lines. Clamps 23 and 24 can be independently operated by control means (not shown).

Manifold 12 has a main conduit with an inlet portion 30, a helical portion 31 and an outlet portion 32. A debubbler portion 33 is located between helical portion 31 and outlet portion 32. Debubbler 33 is primarily a passage of larger internal diameter than the outlet portion 32 and is positioned in a vertical direction. Debubbler 33 communicates with an outlet for spent liquid, such as a drain, through line 34.

A supply 25 for an anti-coagulant solution is connected through line 26 to channel 14 of pump 11. Channel 14 is connected in turn through line 27 to one lumen of double lumen cannula 10. This anti-coagulant mixes with blood 28 entering the cannula 10 from a blood vessel of the subject (not shown) and the resultant mixture leaves the cannula through line 29 which communicates with channel 15 of pump 11. Pump channel 15 communicates through line 35 to inlet portion 30 of manifold 12.

A supply 36 for a buffer solution is connected through line 37 to channel 16 of pump 11 which is in turn connected through line 38 to inlet portion 30 of manifold 12.

A supply 39 for a gas, such as air, which is non-reactive with the blood, anti-coagulant or buffer is connected through line 40 to channel 17 of pump 11 which is in turn connected through line 41 to inlet portion 30 of manifold 12.

The gas from supply 39 aids in mixing the buffer from supply 36 with the blood sample from cannula 10. Passage of the total mixture segmented by gas bubbles through the helical portion 31 of manifold 12 further aids in obtaining a desired uniform liquid mixture. When this mixture enters the debubbler 33, the gas passes upward and is thus separated from the liquid mixture which flows through outlet portion 32 of manifold 12. The gas is then exhausted through line 34. The manifold outlet 32 is connected through line 42 to sensor 13. The liquid outlet of sensor 13 is connected through line 43 to channel 18 of pump 11 which is in turn connected through line 44 and line 34 to the drain. Lines 42 and 43 constitute a sensor flow path means.

Pump channels 15, 16 and 17 thus provide pumping pressure to provide a liquid sample to debubbler 33. Pump channel 18 provides the suction conditions to draw the liquid sample through sensor 13 and to pump the spent liquid sample to the drain. The electrical output of sensor 13 is connected through line 46 to a read-out means 45 which can be a display, a printer or a controller which controls additional circuits (not shown) based upon the output of sensor 13.

From time to time it is necessary to calibrate or check the calibration of sensor 13. A supply 47 of a first base-line reference liquid, containing zero or controlled low amount of a particular material such as glucose, is connected through line 48 to channel 19 of pump 11 which is then in turn connected through line 49 to line 42. A supply 50 of a second high level reference liquid, containing a controlled high amount of a particular material such as glucose, is connected through line 51 to channel 20 of pump 11 which is then in turn connected through line 52 to line 42. In order to calibrate sensor 13 to a base-line reading, clamps 23 are removed from channel 19 and pumping action is started for this channel of the pump allowing first base-line reference liquid to be pumped from supply 47 to line 42 leading to sensor 13. The flow rate and resultant pressure of the first base-line reference liquid through channel 19 is greater than the flow rate of pump channel 18 which withdraws liquid from sensor 13 and thus is greater than the flow rate and resultant pressure of the liquid sample from outlet 32. The amount of first base-line reference liquid in excess of the amount passing through sensor 13 then passes through the debubbler 33 directly to the drain. The continuously flowing liquid sample coming from the cannula along with the buffer solution from supply 36 cannot pass into line 42 so they are diverted away from the sensor 13 and also pass through the debubbler 33 to the drain. Appropriate controls (not shown) associated with sensor 13 and read-out means 45 are then adjusted so that the read-out means indicates a material level identical to that of the first base-line reference liquid. As soon as sensor 13 is properly calibrated to the first base-line reference level, clamps 23 are then applied to channel 19 and the pumping action is stopped for this channel to stop flow of first base-line reference liquid from supply 47. In order to calibrate sensor 13 to a second high reference level, clamps 24 are removed from channel 20 and pumping action is started for this channel of the pump allowing second high level reference liquid to be pumped from supply 50 to line 42 leading to sensor 13. The flow-rate and resultant pressure of the second high level reference liquid through channel 20 is likewise greater than the flow rate and resultant pressure of the liquid sample and it acts to divert any liquid sample from flowing to the sensor 13. Appropriate controls are adjusted so that the read-out means indicates a material level identical to that of the second high level reference liquid. As soon as sensor 13 is properly calibrated to the second high reference level, clamps 24 are then applied to channel 20 and the pumping action is stopped for this channel to stop flow of the second high level reference liquid from supply 50. Flow of the liquid sample from cannula 10 to sensor 13 is then automatically resumed. Pump channels 19 and 20 along with associated piping, clamps and pumping action controls constitute a flow diversion means for diverting the continuously flowing blood sample from the sensor.

It can thus be seen that calibration of the sensor 13 can easily take place without any interference with cannula 10. There is no change in the position of the double lumen components of cannula 10 and thus there is no damage to their sterility condition. The reference solutions in supplies 47 and 50 need not be sterilized since their solutions never come into contact with elements, such as those of cannula 10, which need to maintain sterility conditions.

Figure 2:
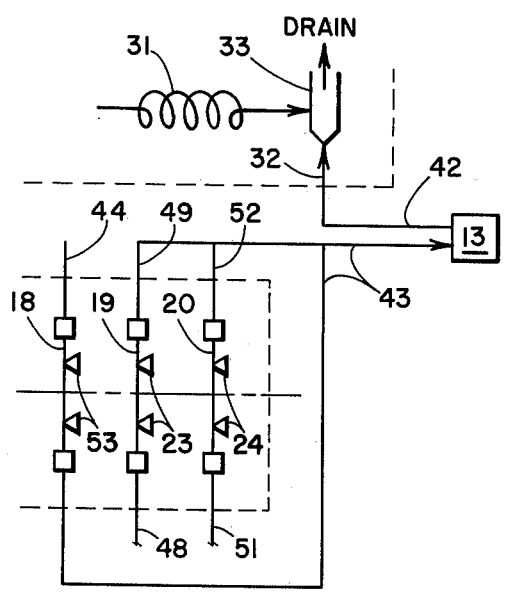
FIG. 2 is a schematic drawing of a portion of the analytical system incorporating another form of the calibration apparatus of the present invention.

In the above calibration apparatus circuitry, the reference liquids pass through the sensor 13 and the sensor flow path in the same direction as the normal flow of the liquid sample from the cannula 10. Another calibration apparatus variation is shown in FIG. 2 wherein the reference liquids pass through the sensor 13 and the sensor flow path in a direction opposite to that of the normal flow of the liquid sample from the cannula 10. In this variation lines 49 and 52 from pump channels 19 and 20 are connected to line 43 and clamps 53 are provided on pump channel 18. When it is desired to contact sensor 13 with the appropriate reference liquid, the appropriate clamps 23 or 24 are released, the appropriate pump channel pumping action is started, clamps 53 are applied to channel 18 and the pumping action for channel 18 is stopped. Pump channel 18 then ceases to remove any liquid from line 43. Since pump channel 18 has stopped, there is no suction applied to outlet 32 and thus any flow of liquid sample from helical portion 31 to outlet 32 is only by gravity. Pump channel 19 or 20 then pumps the appropriate reference liquid through sensor 13 and out through line 42 to debubbler 33 and on to the drain. The low flow rate of the liquid sample entering outlet 32 from the helical portion 31 has a lower pressure than the reference liquid from line 42 and is prevented from contacting sensor 13. It also flows through debubbler 33 to the drain. This apparatus variation has the advantage of requiring a lower flow of reference liquids for calibration than the apparatus of FIG. 1.

It should be noted that while the apparatus of FIGS. 1 and 2 used two separate pumping channels 19 and 20 for the two reference liquids, it is understood that a single pumping channel can be used with a selector valve (not shown) to determine whether supply 47 or supply 50 is to be connected to the single pump channel.

In the above calibration apparatus and operating procedures, the concentration of the glucose, for example, in the second high level reference liquid in supply 50 is selected so that the read-out of the sensor 13 will represent the results from a predetermined sample dilution. For example, if the blood sample 28 entering cannula 10 is intended to be diluted by the anti-coagulant material from supply 25 and a buffer solution from supply 36 in an amount of six volumes of diluent per volume of blood sample, then the concentration of the second reference liquid is chosen so that the sensor 13 read-out represents a similar dilution. For example, if the actual concentration of glucose in the second reference liquid is 20 mg. percent and a 7:1 diluent ratio is assumed, then the sensor 13 readout should be 140 mg. percent. So long as the actual dilution of the sample 28 is 7:1, the calibration will provide correct output readings. However, if the actual dilution, due to variations in apparatus tolerances, is different from 7:1, the readings will be in error. In order to calibrate the sensor 13 to the actual dilution taking place in the apparatus, the following procedures should be followed. A calibration sample of blood identical to that of sample 28 is diluted to the same intended dilution ratio employed in the above calibration procedure (7:1). The sensor 13 is then contacted with this diluted calibration sample and the read-out value is noted. Sensor 13 is then contacted with the normal sample flowing from cannula 10 to line 42 and the read-out value is noted. If this value is the same as that obtained for the above diluted calibration sample, then the actual dilution obtained by the apparatus is 7:1. However, if the actual dilution is different from 7:1, there will be a difference in the reading. The sensor output from the actual sample plus dilution is then adjusted to read the same value as that obtained from the calibration sample. This will compensate the readings for variations in dilution. In this procedure the calibration sample can also be considered a reference liquid.

Figure 3:
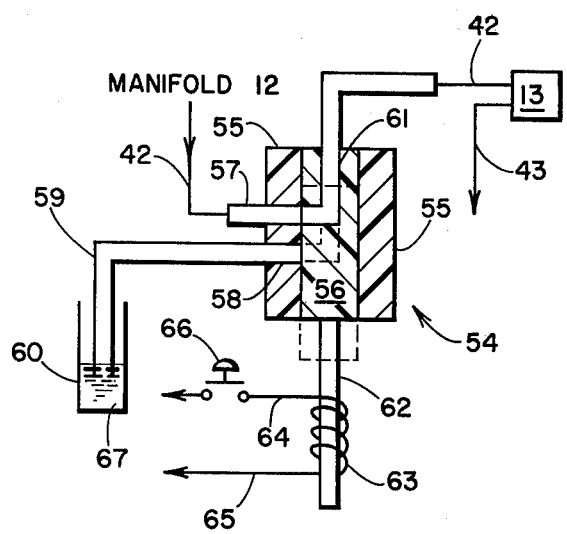
FIG. 3 is a schematic drawing of a portion of the analytical system incorporating still a further form of the calibration apparatus of the present invention.

An apparatus configuration for accomplishing this calibration is shown in FIG. 3. A valve 54 is placed in line 42 between manifold 12 and sensor 13. This apparatus variation can be used with the apparatus of either FIG. 1 or FIG. 2. When it is used with the apparatus of FIG. 1, it is conveniently located between sensor 13 and the junction of lines 49 and 52 with line 42. Valve 54 is conveniently formed of a sleeve 55 and a core 56 slidably positioned therein. The sleeve has two transverse passages 57 and 58 therein. Passage 57 communicates with line 42 connected to manifold 12. Passage 58 communicates with line 59 which is in turn capable of being placed into a liquid sample receptacle 60. Core 56 has a passage 61 therein which has an axial portion and a radial portion. Core 56 also has an axial extension 62 of magnetic material which is positioned within the winding of a solenoid 63. The leads 64 and 65 of solenoid 63 are connected to a power supply (not shown). Lead 64 has a push-button switch 66 located therein. In normal operation the valve 54 is in the position shown in FIG. 3 wherein passage 61 mates against passage 57. When it is desired to contact sensor 13 with a calibration sample, receptacle 60 containing an appropriate amount of such calibration sample 67 therein is positioned with the end of line 59 immersed therein. Push-button switch 66 is then activated which energizes solenoid 63 to draw the core 56 into the position shown by the dashed lines against the action of suitable spring means (not shown). In this position passage 61 mates against passage 58 and passage 57 is sealed. No liquids from manifold 12 can then reach sensor 13 and sample 67 is drawn through line 59, passages 58 and 61, and line 42 into contact with sensor 13 by the pumping action of pump channel 18 communicating with line 43. Here again the sensor 13 can be calibrated without disturbing the flow of liquid sample from cannula 10. During this calibration procedure, such liquid sample from the cannula flows through the debubbler to the drain.

It is recognized that valve 54 can have a configuration different from that shown in FIG. 3 so long as the desired functions are performed.

It is also understood that the calibration sample used for calibration in the mode shown in FIG. 3 need not be identical to the liquid sample from cannula 10 but could by any other sample desired for calibration purposes.

A preferred configuration for manifold 12 is shown in FIGS. 4 and 5. The manifold body conveniently has two portions 68 and 69 which are attached to each other along an interface 70. Body portion 68 has a stepped axial passage 30 therein and side passages 71, 72 and 73 extending therefrom. Body portion 68 also has an end extension portion 74 with a transverse passage 75 therein. Body portion 69 has an axial passage 32 therein and side passages 76, 77 and 78 extending therefrom. A passage 33 having a larger internal diameter than passage 32 extends vertically from passage 32. A stepped axial passage 82 communicates with passage 33 at a location above passage 32. An axial passage 34 communicates with passage 33 and extends to an end 79 of body portion 69. A side passage 81 communicates with and extends from passage 34. A drain pipe 80 passes through and is supported in passage 75 and communicates with passage 34. A helical conduit 31 surrounds body portion 69 and communicates with stepped axial passage 30 of body portion 68 and with stepped axial passage 82 of body portion 69. The main conduit of manifold 12 comprises inlet portion 30, helical portion 31, passage 82 and outlet portion 32 with debubbler portion 33 located between portions 31 and 32 and communicating with drain 80. Lines 35, 38, 41 and 44 from pump channels 15, 16, 17 and 18, respectively, communicate with side passages 71, 72, 73 and 81 of manifold 12. Lines 49 and 52 from pump channels 19 and 20, respectively, communicate with side passages 76 and 77 of manifold 12. Line 42 from sensor 13 communicates with side passage 78 of manifold 12.

The above description is directed primarily at apparatus for analyzing glucose content of blood. It should be recognized that the invention is not so limited and can be used in any analytical system that requires calibration during use.

What is claimed is:

1. Apparatus for calibration of a sensor during use in a calibratable system for monitoring a specific characteristic of a continuously flowing blood sample comprising in combination a first peristaltic pump means for introducing a continuously flowing blood sample from a source connected thereto; a sensor for detecting said specific characteristic, said sensor having flow path means, said first peristaltic pump means communicating with said sensor flow path means to supply a continuously flowing blood sample thereto; a drain communicating with said sensor flow path means; and a second peristaltic pump means communicating with said sensor flow path means for introducing a reference liquid from a source connected thereto to said sensor flow path means for contact with said sensor, said second pump means being capable when in pumping operation of introducing said reference liquid to said sensor flow path means during sensor calibration at a flow rate and pressure which is greater than the flow rate and pressure of the blood sample in the sensor flow path means from the first peristaltic pump means thus causing a diversion of the continuously flowing blood sample from the sensor to the drain during calibration of the sensor.

2. Apparatus for calibration of a sensor during use in a calibratable system for monitoring a specific characteristic of a continuously flowing blood sample comprising in combination first peristaltic pump means for introducing a continuously flowing blood sample from a source connected thereto; second peristaltic pump means for introducing a buffer solution from a source connected thereto; third peristaltic pump means for introducing a gas from a source connected thereto; a manifold comprising a main conduit having an inlet portion, a helical portion and an outlet portion and a dububbler communicating with said outlet portion, with said helical portion and with an outlet for spent liquid, said inlet portion of said manifold communicating with said first, second and third peristaltic pump means; a sensor for detecting said specific characteristic, said sensor having flow path means, said outlet portion of said manifold conduit communicating with said sensor flow path means to supply a continuously flowing blood sample thereto; fourth peristaltic pump means for introducing a reference liquid from a source connected thereto to said sensor flow path means for contact with said sensor, said fourth pump being capable when in pumping operation of introducing said reference liquid to said sensor flow path means during sensor calibration at a flow and pressure which is greater than the flow rate and pressure of the blood sample in the sensor flow path means from the first peristaltic pump means thus causing a diversion of the continuously flowing blood sample from the sensor to the outlet for spent liquid during calibration of the sensor.

* * * * *